US009980784B2

(12) United States Patent
Fasolino et al.

(10) Patent No.: US 9,980,784 B2
(45) Date of Patent: May 29, 2018

(54) X-RAY INK PEN

(71) Applicant: Raytheon Company, Waltham, MA (US)

(72) Inventors: Stephen T. Fasolino, McKinney, TX (US); William J. Wolfgong, Little Elm, TX (US)

(73) Assignee: RAYTHEON COMPANY, Waltham, MA (US)

( * ) Notice: Subject to any disclaimer, the term of this patent is extended or adjusted under 35 U.S.C. 154(b) by 134 days.

(21) Appl. No.: 15/009,665

(22) Filed: Jan. 28, 2016

(65) Prior Publication Data

US 2017/0215984 A1 Aug. 3, 2017

(51) Int. Cl.

| | |
|---|---|
| ***B43K 29/00*** | (2006.01) |
| ***A61B 90/00*** | (2016.01) |
| ***A46B 11/00*** | (2006.01) |
| ***A61M 35/00*** | (2006.01) |
| ***B43K 8/02*** | (2006.01) |
| ***B43K 8/04*** | (2006.01) |
| ***B43K 8/00*** | (2006.01) |
| ***B43M 11/06*** | (2006.01) |
| ***B43K 7/00*** | (2006.01) |

(52) U.S. Cl.

CPC .......... *A61B 90/39* (2016.02); *A46B 11/0041* (2013.01); *A61M 35/003* (2013.01); *B43K 7/00* (2013.01); *B43K 8/00* (2013.01); *B43K 8/026* (2013.01); *B43K 8/04* (2013.01); *B43M 11/06* (2013.01); *A61B 2090/3933* (2016.02); *A61B 2090/3966* (2016.02)

(58) Field of Classification Search

CPC ............ A61B 90/39; A61B 2090/3966; A61B 2090/3933; B43K 8/026; B43K 8/04; B43K 11/0041

USPC .......................................................... 401/195

See application file for complete search history.

(56) References Cited

U.S. PATENT DOCUMENTS

| | | | |
|---|---|---|---|
| 2,462,018 | A | 2/1949 | Wood |
| 4,813,062 | A | 3/1989 | Gilpatdck |
| 4,831,062 | A | 3/1989 | Gilpatrick |
| 5,323,443 | A | 6/1994 | Lary |
| 2004/0127824 | A1 | 7/2004 | Falahee |
| 2009/0025398 | A1 | 1/2009 | Muller et al. |
| 2011/0097134 | A1 | 4/2011 | Allen et al. |
| 2015/0272702 | A1 | 10/2015 | O'Neill, III et al. |

FOREIGN PATENT DOCUMENTS

JP 01130997 A * 5/1989

OTHER PUBLICATIONS

Notification of Transmittal of the International Search Report and the Written Opinion of the International Searching Authority dated Feb. 24, 2017, 11 pages.

* cited by examiner

*Primary Examiner* — Jennifer C Chiang

(57) ABSTRACT

An apparatus includes a pen. The pen includes a reservoir configured to store a fluid. The pen also includes a tip configured to transfer the fluid from the reservoir onto a surface of an object during writing. The pen further includes a regulator configured to control a flow of the fluid from the reservoir to the tip. The apparatus also includes the fluid stored within the reservoir. The fluid includes a carrier fluid and particles of an X-Ray opaque material.

20 Claims, 4 Drawing Sheets

100
105
120
110
115

X-RAY INK PEN

TECHNICAL FIELD

The present disclosure is directed to systems and methods for x-ray imaging, and more specifically to an X-ray ink pen.

BACKGROUND OF THE DISCLOSURE

There are no commercially available "ink" based pens which can be used to mark objects for X-ray examination which are X-ray opaque. Methods for marking objects for X-ray examination do not enable a user to draw any desired shape or letter, such as fine print.

Certain methods for marking objects only relate to surgical applications, such as surgical film or skin marking. These methods are limited to non-permanent markings. These methods use a heavy metal compound.

Certain methods for marking objects use a waxy medium for dispensing X-ray opaque material, such as a crayon-like marking tool. These methods are limited to applications of applying X-ray opaque marking on textiles.

Certain methods for marking objects use brass stencils for applying the X-ray opaque material. These methods are limited to pre-fabricated shapes and dispensation onto flat surfaces.

Certain methods for marking objects only relate to marking the human body, such as by using a tube. These methods are limited to non-permanent markings in the medical field.

Certain methods for marking objects for X-ray examination include assembling various characters composed of lead (Pb) selected from a lead letter set. These methods typically include the use of toxic metals.

SUMMARY OF THE DISCLOSURE

This disclosure provides an X-Ray Ink Pen.

In a first embodiment, an apparatus includes a pen. The pen includes a reservoir configured to store a fluid. The pen also includes a tip configured to transfer the fluid from the reservoir onto a surface of an object during writing. The pen further includes a regulator configured to control a flow of the fluid from the reservoir to the tip. The apparatus also includes the fluid stored within the reservoir. The fluid includes a carrier fluid and particles of an X-Ray opaque material.

In a second embodiment, a system includes a reservoir configured to store a fluid. The system also includes an applicator configured to receive at least some of the fluid from the reservoir and transfer the obtained fluid onto a surface of an object during a process for applying the obtained fluid onto the surface of the object. The system also includes the fluid stored within the reservoir. The fluid includes a carrier fluid and particles of an X-Ray opaque material.

In a third embodiment, a method includes obtaining a liquid mixture of an amount of carrier fluid and an amount of particles of an X-Ray opaque material. The method also includes storing at least some of the obtained liquid mixture in a reservoir. The reservoir is associated with an applicator configured for applying the obtained liquid mixture onto a surface of an object to be X-rayed.

Although specific advantages have been enumerated above, various embodiments may include some, none, or all of the enumerated advantages. Additionally, other technical advantages may become readily apparent to one of ordinary skill in the art after review of the following figures and description.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

It should be understood at the outset that, although example embodiments are illustrated below, the present invention may be implemented using any number of techniques, whether currently known or not. The present invention should in no way be limited to the example implementations, drawings, and techniques illustrated below. Additionally, the drawings are not necessarily drawn to scale.

Figure 1A:
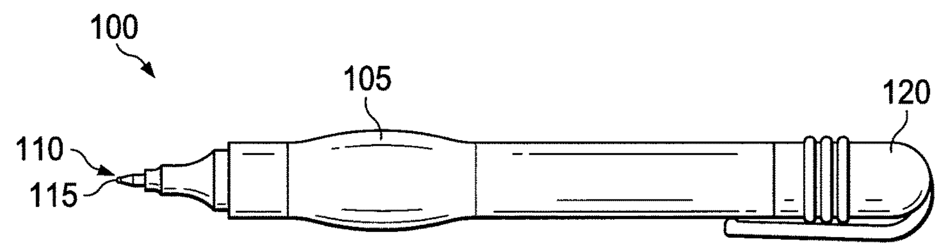
FIGS. 1A and 1B illustrate examples of an X-Ray ink pen according to embodiments of this disclosure.
Figure 1B:
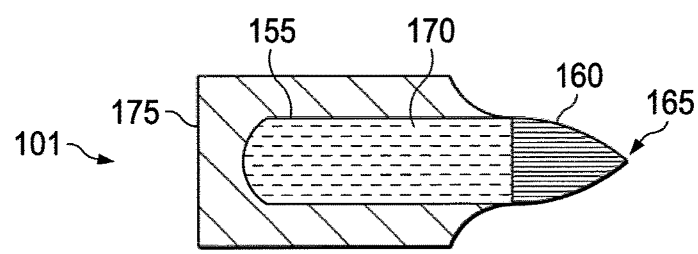

FIGS. 1A and 1B illustrate examples of an X-Ray ink pen 100-101 according to embodiments of this disclosure. The X-Ray ink pens 100-101 of FIGS. 1A and 1B include systems for applying X-Ray opaque liquid onto a surface of an object to be X-ray imaged. The embodiments of the X-Ray ink pen 100-101 shown in FIGS. 1A and 1B are for illustration only. Other embodiments could be used without departing from the scope of the present disclosure.

The X-Ray ink pens 100-101 allow users to mark objects prior to submission for X-ray evaluation. For example, the X-Ray ink pens 100-101 can be used to highlight areas of interest or add descriptive marking that would be depicted in X-ray images in a manner visible to an unaided human eye. That is, the X-Ray ink pens 100-101 enable a user to quickly dispense X-ray ink in a desired shape, such as a letter or number or drawn shape. A user can write or draw with the X-Ray ink pens 100-101 in a manner similar to other writing utensils. The X-Ray ink pens 100-101 do not limit the user to applying the X-ray ink according to conventional pre-fabricated or manufactured shapes or letters. The X-Ray ink adheres to many shapes and contours, and is not limited to flat surfaces. As described more particularly below, the X-Ray ink pens 100-101 can be used in a variety of applications, such as in the electronics field and the medical field. The X-Ray ink pens 100-101 enable X-ray screening of large lots.

As shown in FIG. 1A, the X-Ray ink pen 100 stores in a reservoir 105 a liquid mixture of an amount of carrier fluid and an amount of particles of an X-Ray opaque material (herein referred to as “X-Ray ink”). As an example, the X-Ray ink pen 100 can have the form of a correction fluid pen.

The X-Ray ink pen 100 includes a tip 110 configured to transfer the X-Ray ink from the reservoir 105 onto a surface of an object, such as while writing on the object. The object represents an object that may be later X-ray imaged. For example, the tip 110 can apply the X-Ray ink to the object by physically contacting the surface of the object. The tip 110 can be any suitable size for writing or drawing on a surface of an object to be X-ray imaged. That is, the X-Ray ink pen 100 can have a broad tip (for example, approximately 1.8 millimeters across or greater) or a fine tip (for example, approximately 0.5 millimeters across).

The X-Ray ink pen 100 includes a regulator 115 configured to control a flow of the X-Ray ink from the reservoir 105 to the tip 110. As an example, the X-Ray ink pen 100 can be a ballpoint pen having the ball as the regulator 115, or a ball stop pen. Methods of applying radiopaque material onto human skin via conventional tubes or wax pencils, which limit markings to dollops or broadly formed shapes. The regulator 115 enables X-Ray ink pen 100 to dispense fine strokes by controlling a flow of small molecules within thin liquid X-ray ink. As such, the X-Ray ink pen 100 is not limited to conventional broad strokes or dollop dispensation.

The X-Ray ink pen 100 includes the X-Ray ink that is stored in the reservoir 105. The X-Ray ink includes a carrier fluid and particles of an X-Ray opaque material. That is, the X-Ray ink can be a liquid mixture of an amount of carrier fluid and an amount of particles of an X-Ray opaque material. The ratio of the amount of particles of the X-Ray opaque material to the amount of carrier fluid can span a wide range and is determined based on a number of factors including application contrast requirements, marking dimension requirements, and the ease of application. For example, a ratio of carrier fluid to particles could be 50/50. The reservoir 105 can be loaded with ball bearings or other agitating devices that increase homogenization of the liquid mixture during shaking of the X-Ray ink pens 100-101.

The X-Ray opaque material can be an electrically insulating material (i.e., electrically non-conductive). The characteristic enables the X-ray ink to be applied onto electrical circuit elements or connections without creating short circuit paths to the electronics. The X-Ray opaque material can be non-toxic to humans. The characteristic enables the X-ray ink to be applied onto be drawn onto the skin of a person without harming the person. The X-Ray opaque material can be chemically inert, namely non-reactive. This characteristic enables the X-ray ink to be applied onto surfaces of various compositions without causing a chemical reaction with the surface onto which it is applied. For example, the chemically inert characteristic enables the X-ink to be applied onto the surface of electrical circuit elements or connections without causing a chemical reaction with the electronics which may destruct the hardware. In certain embodiments, the X-Ray opaque material is an electrically insulating material that is non-toxic to humans and chemically inert. Examples of electrically insulating, non-toxic, and chemically inert X-Ray opaque material include: bismuth oxide (also referred to as “$Bi_2O_3$” or “Bismuth (III) Oxide” or “bismuth trioxide”), or other high density compounds that are electrically insulating, non-toxic to humans, and chemically inert. The X-Ray ink remains stable within an operating temperature range of the object onto which the fluid is applied. For example, under typical ambient conditions, the X-Ray ink can be applied to a surface of an object, such as a microcontroller, can be allowed to set-up (for example, to cure, to dry, and the like) on the surface of the object in order be stable on the surface of the object, and after becoming stable on the object, can remain stable or otherwise viable, for an example, the ink will not melt, within an operating range of −50° C. to 80° C. The particles of the X-Ray opaque material have a diameter within a predetermined range, such as having a diameter less that a predetermined maximum diameter. The predetermined maximum diameter can be the size of the smallest opening through which the X-Ray ink flows between the reservoir 105 and the tip 110. For example, particles of the X-Ray opaque material can be a nanopowder, including nanospheres each having a diameter in the range of 90-200 nanometers. The viscosity of the X-Ray ink is affected by the ratio of the mixture of carrier and the size of the particles of the X-Ray opaque material, such that smaller particles increase the viscosity, and larger particles decrease the viscosity. When the same mass of smaller sized particles are added to a fluid, the number of particle-particle interactions increases, resulting in increased viscosity. As a non-limiting example, X-Ray ink that remains stable in the operating range of −50° C. to 80° C. can be formed by mixing nano-sized bismuth oxide as the particles of X-Ray opaque material with nitrocellulose as the carrier fluid according to the 50/50 mixing ratio.

Note that certain X-Ray opaque materials are toxic to humans, such as lead (Pb) or barium (Ba) compounds. Note that certain X-Ray opaque materials are not chemically inert, but instead are chemically reactive, such as iodates, iodides, and certain salts. Note that certain X-Ray opaque materials are not characterized as an electrically insulating material, such as iodides. Unlike conventional radiopaque marking devices, the X-Ray ink pen 100 of this disclosure uses an X-Ray opaque material that is electrically insulating, non-toxic to humans, and chemically inert. The electrically insulating characteristic enables the X-Ray pen 100 to be used in electronic, circuit cards, or hardware application. As such, the X-Ray pen 100 is not limited to conventional surgical applications (for example, surgical film or skin marking).

Examples of the carrier fluid include a nitrocellulose material, a water-soluble material, or an epoxy material. The carrier fluid can be permanent once written or drawn onto the surface of the object to be X-ray imaged, such as the epoxy material. The carrier fluid can be semi-permanent, such as the nitrocellulose material, which may require a solvent for removal from the surface of the object to be X-ray imaged. The carrier fluid can be removable, such as a water-soluble material, which allows for easy clean up. The carrier fluid can allow the particles of the X-Ray opaque material to be suspended or dissolved.

Unlike conventional radiopaque marking devices, the X-Ray ink pen 100 of this disclosure uses a carrier fluid material that remains stable within an operating temperature range. The temperature resilient characteristic of the X-Ray ink 170 enables the X-Ray pen 100 to be used in an operating temperature range of electronic, circuit cards, or hardware application. As such, the X-Ray pen 100 is not limited to conventional textile applications, wherein the application of radiopaque material via a waxy medium (e.g. crayon tool) would melt within the operating temperature range or otherwise destabilize.

The X-Ray ink pen 100 includes a cap 120. The cap 120 can fit, snap, or otherwise be secured onto a bottom end of the exterior of the body of the X-Ray ink pen 100. This feature prevents loss of the cap 120 when the writing portion of the X-Ray ink pen 100 is not enclosed by the cap 120. The cap 120 can be secured onto an upper portion of the X-Ray ink pen 100 in order to enclose the tip 110 and other writing portion of the X-Ray ink pen 100, reducing exposure of the tip 110 to air, which may dry fluid.

FIG. 1B shows that the X-Ray ink pen 101 can have the form of a brush tip pen according to embodiments of this disclosure. The X-Ray ink pen 101 includes a reservoir 155 and an applicator 160, which includes the tip 165 of the X-Ray ink pen 101.

The reservoir 155 is configured to store a fluid, such as X-Ray ink 170. The reservoir 155 can be an elongated cylindrical tube enclosed within the housing 175 of the body of the X-Ray ink pen 101.

The applicator 160 is configured to transfer the X-Ray ink 170 from the reservoir 155 to the surface of an object to be X-ray imaged. The applicator 160 can be a brush, such as a bristle brush or a foam brush. The applicator 160 can be any suitable mechanism for writing or drawing on the surface of the object to be X-ray imaged using some of the X-Ray ink 170 from the reservoir 155.

Although FIGS. 1A and 1B illustrate certain example X-Ray ink pens 100-101, various changes may be made to FIGS. 1A and 1B. For example, a portion of the housing 175 or reservoir 155 could include flexible material enabling a user to squeeze the X-Ray ink pen 101 to force the X-Ray ink out of the reservoir 155 at a faster rate than its flow rate due to gravity alone. The flexible material portion of the housing 175 could have a wider diameter than the remainder of the housing 175. In certain embodiments, the portion of the housing 175 composed of the flexible material could be disposed proximate walls of the reservoir 155, the flexible material reduces a volume of the reservoir by deforming upon an application of an inward-squeeze pressure. During the deformation of the flexible material, the flexible material transfers at least some of the inward-squeeze pressure against one or more opposing walls of reservoir, causing the one or more opposing walls to move closer to each other. During the deformation of the flexible material, the volume rejection of the reservoir forces the X-Ray ink 170 out of the reservoir toward the tip 110. A release of the inward-squeeze pressure restores a non-deformed state of the X-Ray ink pen 101, wherein X-Ray ink 170 exits the reservoir at a flow rate according to gravity and orientation of the X-Ray ink pen 101.

Figure 2:
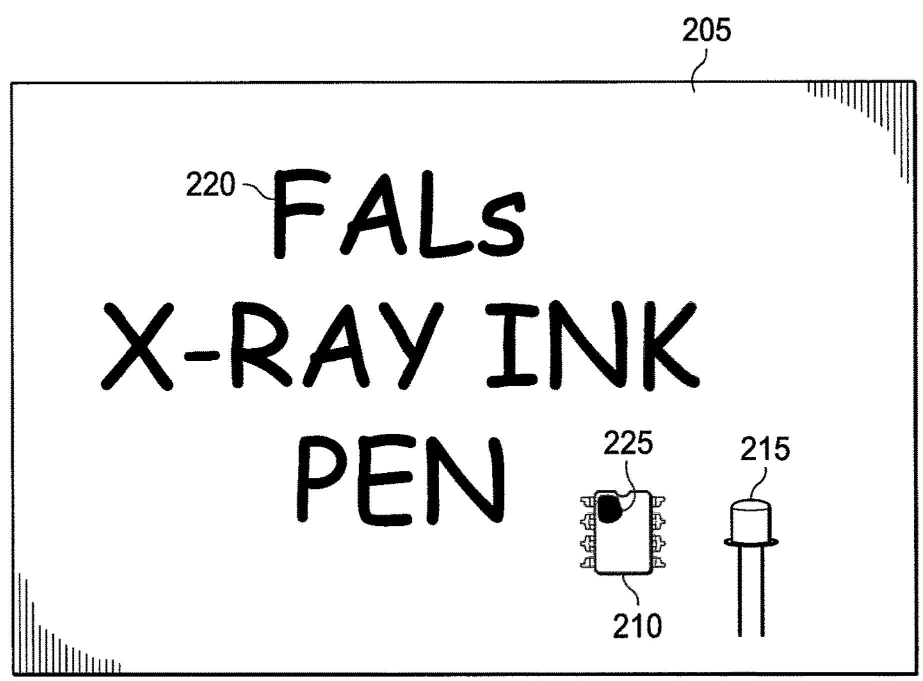
FIG. 2 illustrates X-Ray ink according to embodiments of this disclosure applied to the surface of various objects to be X-ray imaged.

FIG. 2 illustrates the X-Ray ink according to embodiments of this disclosure applied to the surface of various objects to be X-ray imaged. In some embodiments, a user can use the X-Ray ink pen 100 during a process for applying X-Ray ink onto a surface of the objects to be X-ray imaged.

In the example shown, the X-Ray ink includes nano-sized bismuth oxide. Also in the example shown, objects to be X-ray imaged include a sheet of paper 205, and two different styles of Integrated Circuit (IC) Package 210 and 215. X-Ray ink 220 was applied onto the surface of the sheet of paper 205 by writing "FALs X-RAY INK Pen" using the X-Ray ink pen 100. The X-Ray ink 225 was applied onto the surface of the IC package 210 by drawing the shape of a dot using the X-Ray ink pen 100. The surface of the IC package 215 does not have X-Ray ink applied.

Figure 3A:
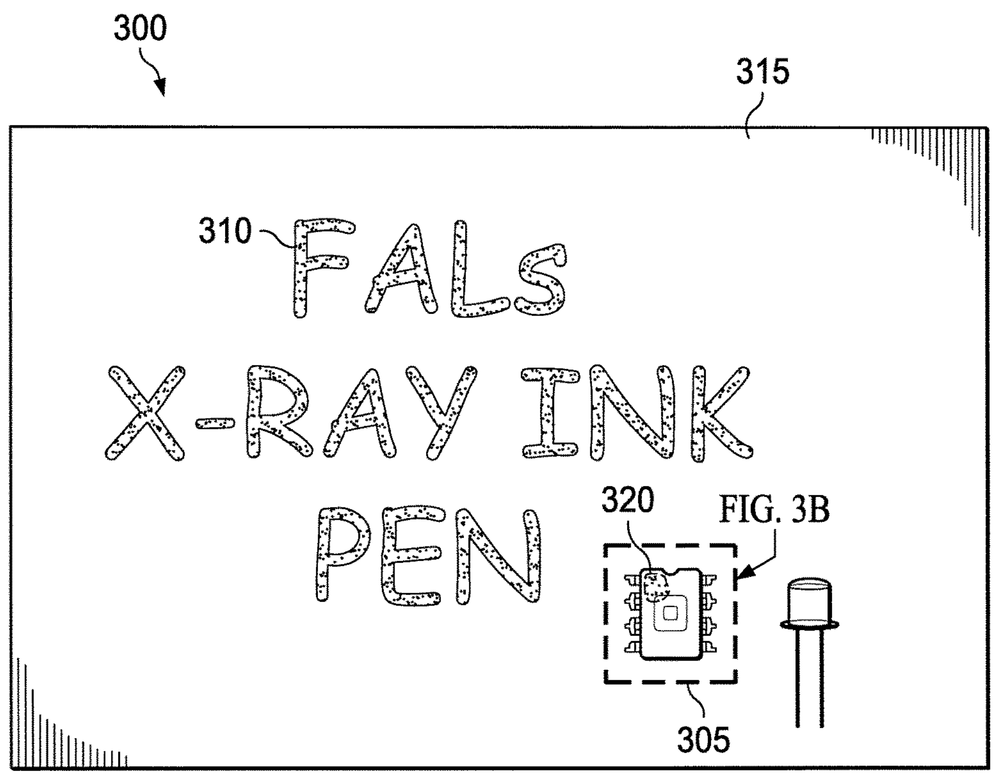
FIGS. 3A and 3B illustrate an X-Ray image of various objects in FIG. 2.
Figure 3B:
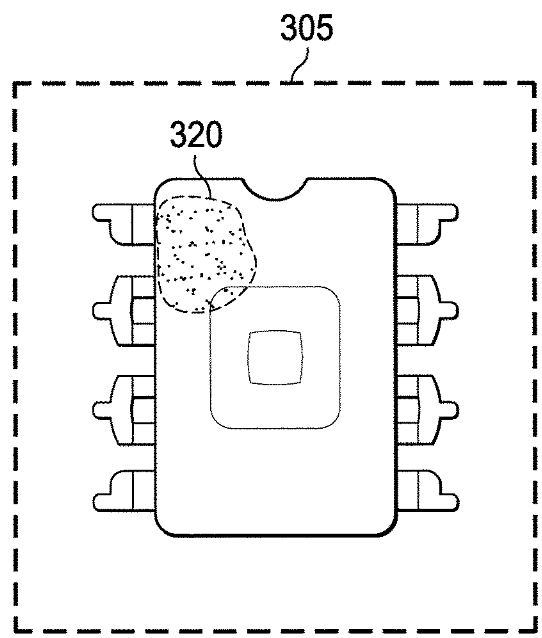

FIGS. 3A and 3B illustrate an X-Ray image 300 of various objects in FIG. 2. A portion 305 of the X-Ray image 300 depicts the IC package 210. As shown in FIG. 3A, when the X-Ray ink 220 is X-Ray imaged or otherwise exposed to X-rays, it appears as a darker area 310 in contrast to the light shade 315 of the X-ray imaged paper.

FIG. 3B illustrates a zoomed-in view of the portion 305 of the X-Ray image 300 that depicts the IC package 210. As shown, when the X-Ray ink 220 is X-Ray imaged, it appears as a darker area 320 (with emphasis added in the form of a surrounding by a lighter dashed line) in contrast to other areas of the IC package 210 that do not have X-Ray ink 225 applied.

Figure 4:
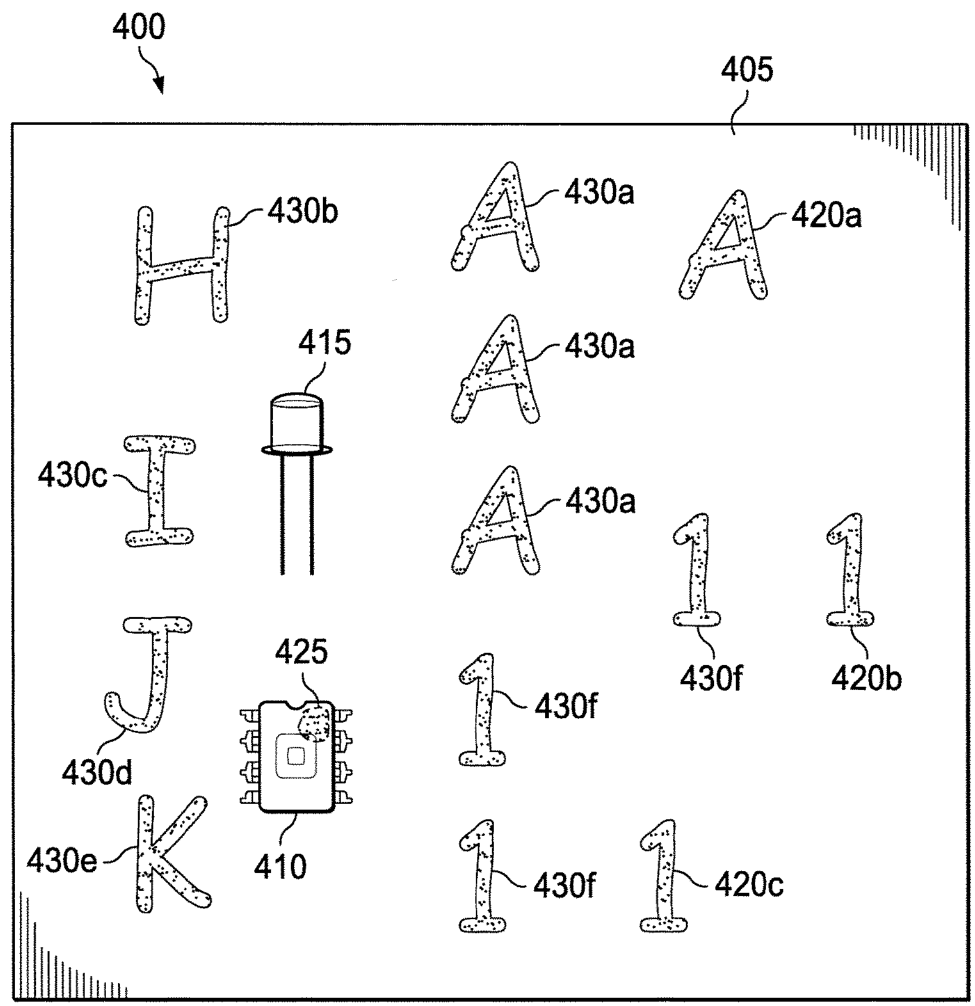
FIG. 4 illustrates an X-Ray image of various objects that were X-ray imaged after different X-Ray inks were applied to surfaces of the various objects using an X-Ray ink pen according to embodiments of this disclosure.

FIG. 4 illustrates an X-Ray image 400 of various objects that were X-ray imaged after different X-Ray inks were applied to the surfaces of the various objects using an X-Ray ink pen according to embodiments of this disclosure. In some embodiments, a user can use the X-Ray ink pen 100 during a process for applying X-Ray ink onto surfaces of the objects in X-ray image 400.

In the example shown, objects to be X-ray imaged include a sheet of paper 405, an IC 410, and a different type of IC 415. Bismuth oxide X-Ray ink 420*a*-420*c* is applied onto the surface of the sheet of paper 405 by writing various characters (indicated by arrows) such as "A" and "1" using the X-Ray ink pen 100. Bismuth oxide X-Ray ink 425 (shown as a darker area surrounded by a lighter dashed line) is applied onto the surface of the IC 410 by drawing the shape of a dot using the X-Ray ink pen 100. The surface of the IC 415 does not have X-Ray ink applied.

For purpose of a performance comparison of the bismuth oxide X-Ray ink to a liquid mixture of bismuth iodide, bismuth iodide 430 is applied onto the surface of the sheet of paper 405 by writing various characters, such as "A" 430*a*, "H" 430*b*, "I" 430*c* "J" 430*d* "K" 430*e* and "1" 430*f* using the X-Ray ink pen 100. The bismuth oxide X-Ray ink can be dispensed according to a finer writing stroke, as opposed to the coarser dispensation of the bismuth iodide 430.

Figure 5:
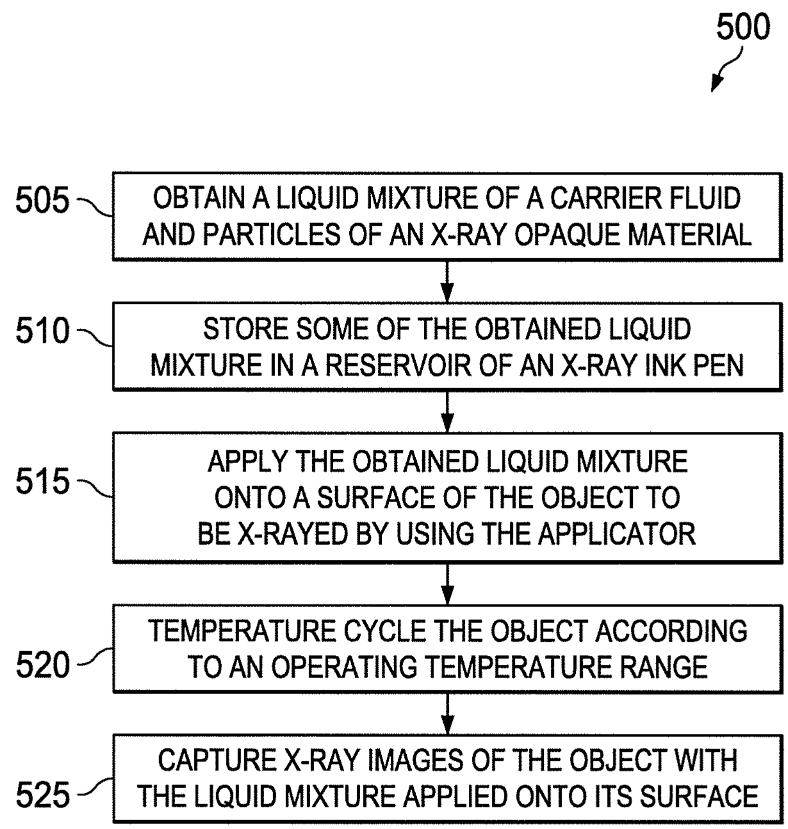
FIG. 5 illustrates a method of manufacturing and testing an X-Ray ink pen according to embodiments of this disclosure.

FIG. 5 illustrates a method 500 of manufacturing and testing an X-Ray ink pen according to embodiments of this disclosure. The embodiment of the method 500 shown in FIG. 5 is for illustration only. Other embodiments could be used without departing from the scope of the present disclosure. The method 500 can be implemented by a manufacturing plant that includes machines controlled by one or more computers. For example, the X-ray ink pens 100-101 can be manufactured and tested by the manufacturing plant implementing the method 500. For ease of explanation, FIG. 5 will be described as if the IC package 210 of FIG. 2 is the object to be X-rayed, though other objects can be used.

At block 505, a liquid mixture of a carrier fluid and particles of an X-Ray opaque material (herein referred to as "X-Ray ink") are obtained. For example, the manufacturing plant can obtain the X-Ray ink by mixing the carrier fluid with the particles of the X-Ray opaque material. In certain embodiments, the manufacturing plant can obtain the X-Ray ink by receiving a mixture of a carrier fluid and particles of an X-Ray opaque material. The manufacturing plant can adjust the ratio of carrier fluid and particles of an X-Ray opaque material according to the dimensions of the flow path of the X-Ray ink pen.

At block 510, some of the obtained liquid mixture is stored in a reservoir with an applicator. For example, the manufacturing plant can add some of the X-Ray ink to one or more reservoirs 105, 155. The manufacturing plant can store some of the obtained X-Ray ink in a reservoir 105, 155 associated with an applicator 160 and process for applying the obtained X-Ray ink onto a surface of the IC package 210 to be X-rayed. The reservoir 105, 155 can be coupled to a writing portion of the X-Ray ink pen, or the manufacturing plant can connect the reservoir 105, 155 to the writing portion (including the regulator 115 and tip 110), enabling the X-Ray ink to flow from the reservoir 105 to the tip 115.

At block 515, the obtained liquid mixture is applied onto a surface of the object to be X-rayed by using the applicator.

For example, the manufacturing plant can include a robotic arm that places the tip 110 of the X-Ray ink pen in contact with the surface of the IC package 210. The manufacturing plant can move the X-Ray ink pen according to six degrees of freedom to write or draw on the surface of the IC package 210, for example up or down vertical movement adjusts the amount of force that the tip 110 applies to the surface of the IC package 210.

At block 520, after the ink is applied to the object, the object is temperature cycled according to an operating temperature range. For example, the manufacturing plant can expose the IC package 210 (e.g., an assembly) to −50° C. and 80° C. and any other temperature within the operating temperature range of the IC package 210. As a specific non-limiting example, once the X-Ray ink has set-up on the IC package 210 surface or otherwise become stable on the IC package 210 surface, the X-Ray ink does not melt or deform within its operating range of −50° C. to 80° C. This temperature cycling test provides evidence that the X-Ray ink maintains the characteristics of being electrically insulating, non-toxic to humans, and chemically inert during operation of the object onto which it may be permanently applied. This temperature cycling test can be used to ensure that the X-ray ink does not negatively affect the object within the operating temperature range of the IC package 210.

At block 525, X-ray images of the object are captured with the liquid mixture applied onto its surface after setting. For example, the manufacturing plant can capture an X-Ray image of the IC package 210 with the X-Ray ink applied to its surface. This X-Ray imaging test provides evidence that in an X-Ray image, the X-Ray ink provides adequate contrast in comparison to unmarked portions of the IC package 210, or alternatively indicates that the mixture should be adjusted.

Although FIG. 5 illustrates one example method 500 of manufacturing and testing an X-Ray ink pen, various changes may be made to FIG. 5. For example, in block 515, a person can use the X-Ray pen 100, 101 to write or draw on the surface of an electric circuit board.

Modifications, additions, or omissions may be made to the systems, apparatuses, and methods described herein without departing from the scope of the invention. The components of the systems and apparatuses may be integrated or separated. Moreover, the operations of the systems and apparatuses may be performed by more, fewer, or other components. The methods may include more, fewer, or other steps. Additionally, steps may be performed in any suitable order. As used in this document, "each" refers to each member of a set or each member of a subset of a set.

To aid the Patent Office, and any readers of any patent issued on this application in interpreting the claims appended hereto, applicants wish to note that they do not intend any of the appended claims or claim elements to invoke 35 U.S.C. Section 112(f) as it exists on the date of filing hereof unless the exact words "means for" or "step for" are explicitly used in the particular claim.

What is claimed is:

1. An apparatus comprising:
a pen including:
a reservoir configured to store a fluid,
a tip configured to transfer the fluid from the reservoir onto a surface of an object during writing,
a regulator configured to control a flow of the fluid from the reservoir to the tip, and
a housing including a flexible material disposed proximate to one or more walls of the reservoir, the flexible material configured to reduce a volume of the reservoir by deforming upon application of an inward squeeze and force at least some of the fluid out of the reservoir toward the tip; and
the fluid stored within the reservoir, the fluid comprising:
a carrier fluid, and
particles of an X-Ray opaque material.

2. The apparatus of claim 1, wherein the X-Ray opaque material is non-toxic to humans.

3. The apparatus of claim 1, wherein the X-Ray opaque material is chemically inert.

4. The apparatus of claim 1, wherein the X-Ray opaque material is an electrically non-conductive material.

5. The apparatus of claim 1, wherein the X-Ray opaque material includes bismuth oxide.

6. The apparatus of claim 1, wherein the carrier fluid comprises at least one of:
a nitrocellulose material,
a water-soluble material, or
an epoxy material.

7. The apparatus of claim 1, wherein the particles have a diameter within a predetermined range.

8. The apparatus of claim 1, wherein the fluid is stable within a temperature range of −50° to 80° Celsius.

9. A system comprising:
a reservoir configured to store a fluid;
an applicator configured to receive at least some of the fluid from the reservoir and transfer the received fluid onto a surface of an object during a process for applying the obtained received fluid onto the surface of the object;
a housing including a flexible material disposed proximate to one or more walls of the reservoir, the flexible material configured to reduce a volume of the reservoir by deforming upon application of an inward squeeze and force the at least some of the fluid from the reservoir toward the applicator; and
the fluid stored within the reservoir, the fluid comprising:
a carrier fluid, and
particles of an X-Ray opaque material.

10. The system of claim 9, wherein the X-Ray opaque material is non-toxic to humans.

11. The system of claim 9, wherein the X-Ray opaque material is chemically inert.

12. The system of claim 9, wherein the X-Ray opaque material is an electrically non-conductive material.

13. The system of claim 9, wherein the X-Ray opaque material includes bismuth oxide.

14. The system of claim 9, wherein the carrier fluid comprises at least one of:
a nitrocellulose material,
a water-soluble material, or
an epoxy material.

15. The system of claim 9, wherein the particles have a diameter within a predetermined range.

16. The system of claim 9, wherein the fluid is stable within a temperature range of −50° to 80° Celsius.

17. A method comprising:
obtaining a liquid mixture of an amount of carrier fluid and an amount of particles of an X-Ray opaque material; and
storing at least some of the obtained liquid mixture in a reservoir associated with an applicator configured for applying the obtained liquid mixture onto a surface of an object to be X-rayed;
wherein one or more walls of the reservoir are disposed proximate to a flexible material, the flexible material configured to reduce a volume of the reservoir by deforming upon application of an inward squeeze to force at least some of the liquid mixture out of the reservoir toward the applicator.

18. The method of claim 17, wherein the X-Ray opaque material is:

non-toxic to humans;

chemically inert; and an electrically insulating material.

19. The method of claim 17, wherein the X-Ray opaque material includes bismuth oxide.

20. The method of claim 17, wherein the liquid mixture is stable within a temperature range of −50° to 80° Celsius.

* * * * *